United States Patent
Zhang et al.

(10) Patent No.: US 9,290,431 B2
(45) Date of Patent: Mar. 22, 2016

(54) PROCESS FOR PREPARATION OF HIGHLY PURE, NON-YELLOWING METHACRYLIC ACID

(71) Applicants: Zhengfeng Zhang, Shanghai (CN); Gerhard Koelbl, Gernsheim (DE); Lorenza Sartorelli, Ober-Ramstadt (DE); Horst Hiltner, Muenster (DE); Huisheng Wang, Shanghai (CN); Mirko Michel, Dortmund (DE)

(72) Inventors: Zhengfeng Zhang, Shanghai (CN); Gerhard Koelbl, Gernsheim (DE); Lorenza Sartorelli, Ober-Ramstadt (DE); Horst Hiltner, Muenster (DE); Huisheng Wang, Shanghai (CN); Mirko Michel, Dortmund (DE)

(73) Assignee: EVONIK RÖHM GmbH, Darmstadt (DE)

( * ) Notice: Subject to any disclaimer, the term of this patent is extended or adjusted under 35 U.S.C. 154(b) by 0 days.

(21) Appl. No.: 14/397,295

(22) PCT Filed: Apr. 22, 2013

(86) PCT No.: PCT/EP2013/058289
§ 371 (c)(1),
(2) Date: Oct. 27, 2014

(87) PCT Pub. No.: WO2013/164216
PCT Pub. Date: Nov. 7, 2013

(65) Prior Publication Data
US 2015/0126777 A1     May 7, 2015

(30) Foreign Application Priority Data
May 3, 2012  (WO) ................ PCT/CN2012/075033

(51) Int. Cl.
*C07C 51/47* (2006.01)
*C07C 51/43* (2006.01)
*C07C 51/44* (2006.01)
*C07C 51/48* (2006.01)

(52) U.S. Cl.
CPC ................ *C07C 51/47* (2013.01); *C07C 51/43* (2013.01); *C07C 51/44* (2013.01); *C07C 51/48* (2013.01)

(58) Field of Classification Search
None
See application file for complete search history.

(56) References Cited

U.S. PATENT DOCUMENTS

| 3,658,886 | A | 4/1972 | Sennewald et al. |
| 4,879,412 | A | 11/1989 | Iwasaki et al. |
| 5,959,142 | A | 9/1999 | Wakimura et al. |
| 2010/0273970 | A1 | 10/2010 | Koestner et al. |

FOREIGN PATENT DOCUMENTS

| CN | 86102590 | A | | 1/1987 |
| CN | 101497563 | A | | 8/2009 |
| EP | 0 710 643 | | | 5/1996 |
| EP | 710643 | | * | 5/1996 |
| EP | 2 085 376 | | | 8/2009 |
| EP | 2085376 | | * | 8/2009 |
| JP | 11 60536 | | | 3/1999 |
| WO | 2010 052079 | | | 5/2010 |

OTHER PUBLICATIONS

International Search Report Issued Jun. 28, 2013 in PCT/EP13/058289 Filed Apr. 22, 2013.
International Search Report Issued Jan. 31, 2013 in priority application PCT/CN12/075033 Filed May 3, 2012.
Notification of the First Office Action in Chinese Patent Application Number: 201380019020.7, issued Nov. 2, 2015, with English translation.

* cited by examiner

*Primary Examiner* — Karl J Puttlitz
(74) *Attorney, Agent, or Firm* — Oblon, McClelland, Maier & Neustadt, L.L.P.

(57) ABSTRACT

This invention relates to a process of preparing highly pure, non-yellowing (meth)acrylic acid necessary for high-tech applications requiring long-tem color stability in the presence of amines. Process for the preparation of highly pure, non-yellowing (meth)acrylic acid comprising the steps: f) Condensation of a (meth)acrylic acid-containing gas phase obtained via a gas phase oxidation process of a C4-compound to generate an aqueous (meth)acrylic acid solution g) Separation of the (meth)acrylic acid from the aqueous (meth)acrylic acid solution to obtain crude (meth)acrylic acid h) Rectification of the crude (meth)acrylic acid to obtain pure (meth)acrylic acid via a sidestream outlet of the rectification column i) Treatment of the pure (meth)acrylic acid generated in step c) with an ion exchange resin j) Distillation of the (meth)acrylic acid generated in step d).

9 Claims, No Drawings

PROCESS FOR PREPARATION OF HIGHLY PURE, NON-YELLOWING METHACRYLIC ACID

CROSS REFERENCE TO RELATED APPLICATIONS

The present application is a 35 U.S.C. §371 national stage patent application of International patent application PCT/EP2013/058289, filed on Apr. 22, 2013, published as WO/2013/164216 on Nov. 7, 2013, the text of which is incorporated by reference, and claims the benefit of the filing date of application no. PCT/CN2012/075033, filed on May 3, 2012, the text of which is also incorporated by reference.

The present invention relates to a process of preparing highly pure, non-yellowing (meth)acrylic acid necessary for high-tech applications requiring long-term color stability.

A variety of processes to produce methacrylic acid are state-of-the-art. Next to synthetic routes starting from $C_2$- or $C_3$-sources, the ACH-Process and the heterogeneously catalysed gas phase oxidation of $C_4$-compounds such as isobutylene, tert-butanol, methacrolein or isobutyl aldehyde are widely in practise. In particular, aldehydes formed as side products in the production of methacrylic acid via the C4 process, absorbing in the UV-range, even at very low concentrations, lead to an undesired yellowing, which in general also generates unacceptable coloration of the resulting application. The extent of coloration of a liquid is usually quantified by means of the APHA-Number, which is often determined by the ASTM Standard D 1209 or via DIN ISO 6271. Processes are thus known in prior art, to reduce this coloration of the methacrylic acid by addition of reagents reacting with such aldehydes.

In this context US 2001/0016668 uses aldehyde treating agents such as aliphatic amines, guanidines, aniline, toluidines or hydrazines to remove color-forming aldehydes from the crude methacrylic acid.

DE 10138150 also suggests aldehyde removing reactants, however, adding them after a first purifying distillation.

WO 2009/095111 generates high-purity methacrylic acid adding decolorisation agents during or before a rectification process with large overhead reflux and small sidestream product withdrawal.

Another purification process described in EP 0169254, particularly for acrylic acid, removes coloring impurities via adding a mercaptane group containing compound in the presence of an acid catalyst. The addition of mercaptanes during the production process of methacrylates, however, always bears the risk of generating problems such as prolonged initiation periods or high residual monomer concentrations during downstream polymerizations.

None of the above mentioned examples of the state-of-the-art generates truly long-term color-stable (meth)acrylic acid. For instance, during tempering at elevated temperatures or after addition of amines or other polymerization accelerators, the thus produced (meth)acrylic acids demonstrate an unacceptable yellowing tendency.

The notation (meth)acrylate, both here and in the total context of the invention, refers to both methacrylate, e.g. methyl methacrylate, ethyl methacrylate, etc., and acrylate, e.g. methyl acrylate, ethyl acrylate, etc., and also mixtures of the two.

The object of the present invention therefore is to avoid or at least diminish the above mentioned deficiencies and to provide a process for the preparation of (meth)acrylic acid with improved long-term color stability and reduced yellowing tendency. An object of the present invention was also to provide a simpler, more efficient and more time- and cost-effective means of improving purity of (meth)acrylic acid, in particular to make it more suitable for use in its downstream products, in particular where as little coloration of the product as possible is preferred.

A contribution to the solution of at least one of the above problems is made by the subject matter of the category-forming claims. The sub-claims dependent on the category-forming claims describe preferred embodiments according to the invention.

A solution to the above objectives is provided by a process for the preparation of highly pure, non-yellowing (meth)acrylic acid comprising the steps:

a) Condensation of a (meth)acrylic acid-containing gas phase obtained via a gas phase oxidation process of a C4-compound to generate an aqueous (meth)acrylic acid solution b) Separation of the (meth)acrylic acid from the aqueous (meth)acrylic acid solution to obtain crude (meth)acrylic acid c) Rectification of the crude (meth)acrylic acid to obtain pure (meth)acrylic acid via a sidestream outlet of the rectification column d) Treatment of the pure (meth)acrylic acid generated in step c) with an ion exchange resin e) Distillation of the (meth)acrylic acid generated in step d)

The C4 compound which is subjected to gas phase oxidation in step a) of the process according to the invention is preferably a C4 compound selected from isobutylene, tert-butyl alcohol and (meth)acrolein, or a mixture of two or more thereof.

The gas phase oxidation in step a) of the process according to the invention preferably occurs in the presence of at least one oxidation catalyst. If the C4 compound is isobutylene or tert-butyl alcohol, the gas phase oxidation to obtain a (meth)acrylic acid-comprising gas phase can occur in one step, whereby one step in this context is considered to mean that initial oxidation to (meth)acrolein and further oxidation to (meth)acrylic acid occur substantially in the same reaction area, in the presence of at least one catalyst. Alternatively, the gas phase oxidation in step a) can occur in more than one step, preferably in two steps, preferably in two or more reaction areas separated from each other, whereby two or more catalysts are preferably present, each catalyst preferably being present in a separate reaction area from each other catalyst. In a two step gas phase oxidation, the first step is preferably at least partial oxidation of the C4 compound to (meth)acrolein, followed by at least partial oxidation of (meth)acrolein to (meth)acrylic acid. Accordingly, for example, in a first reaction step, preferably at least one catalyst suitable for oxidation of at least one C4 compound to (meth)acrolein is present, and in a second reaction step, at least one catalyst suitable for oxidation of (meth)acrolein to (meth)acrylic acid is present.

Suitable reaction conditions for gas phase catalytic oxidation are, for example, temperatures of from about 250° C. to about 450° C., preferably from about 250° C. to about 390° C. and pressures of from about 1 bar to about 5 bar. The space velocity can vary from about 100 to about 6000 $hr^{-1}$ (NTP) and preferably from about 500 to about 3000 $hr^{-1}$. Oxidation, for example gas phase catalytic oxidation, of C4 feeds such as isobutylene to (meth)acrolein and/or (meth)acrylic acid, as well as catalysts therefore, are well known in the literature, for example from U.S. Pat. No. 5,248,819, U.S. Pat. No. 5,231,226, U.S. Pat. No. 5,276,178, U.S. Pat. No. 6,596,901, U.S. Pat. No. 4,652,673, U.S. Pat. No. 6,498,270, U.S. Pat. No. 5,198,579 or U.S. Pat. No. 5,583,084.

Particularly preferred catalysts and processes suitable for oxidation of isobutylene or tert-butanol to (meth)acrolein and/or (meth)acrylic acid are described in EP 0 267 556, and particularly preferred catalysts and processes suitable for oxidation of (meth)acrolein to (meth)acrylic acid are described in EP 0 376 117. These documents are hereby introduced as reference and form part of the disclosure of the present invention.

The gas phase oxidation of (meth)acrolein to (meth)acrylic acid in the process according to the invention preferably occurs at temperatures of from about 250 to about 350° C. and below, at pressures from about 1 to about 3 bar, and at volume loads of from about 800 to about 1800 Nl/l/h.

As oxidising agent, generally oxygen is used, for example, in the form of air, or in the form of pure oxygen or oxygen diluted with at least one gas which is inert under the reaction conditions, such as at least one of nitrogen, carbon monoxide and carbon dioxide, whereby air is preferred as oxidising agent and nitrogen and/or carbon dioxide are preferred as diluent gas. If carbon dioxide is used as diluent gas, this is preferably carbon dioxide recycled from combustion. The gas subjected to gas phase oxidation in step a) of the process according to the invention preferably also comprises water, which is generally present in the form of water vapor. The oxygen, inert gas or gases and water can be introduced into the reaction phase or combined with the C4 compound before or during or before and during the gas phase reaction.

Also in step a) of the process according to the invention, the gas phase which comprises (meth)acrylic acid is condensed to obtain a condensate in the form of an aqueous (meth)acrylic acid-comprising solution. The condensation can occur by any means known to the skilled person and appearing suitable, for example by cooling the (meth)acrylic acid-comprising gas phase to temperatures below the dew point of at least one of its components, in particular of at least one of water and (meth)acrylic acid. Suitable methods of cooling are known to the skilled person, for example, cooling by means of at least one heat exchanger, or by quenching, for example by spraying the gas phase with a liquid, for example with water, an aqueous composition or an organic solvent, such as, for example, aromatic or aliphatic hydrocarbons, or mixtures of at least two thereof, whereby preferred organic solvents have relatively low vapor pressure under the quenching conditions, such as heptane, toluene or xylene, whereby water is preferred according to the invention, and more preferred is at least a portion of the condensate formed in the quenching step. Suitable quenching processes are known to the skilled person, for example from DE 21 36 396, EP 297 445, EP 297 788, JP 01193240, JP 01242547, JP 01006233, US 2001/0007043, U.S. Pat. No. 6,596,901, U.S. Pat. No. 4,956,493, U.S. Pat. No. 4,618,709, U.S. Pat. No. 5,248,819, whose disclosure concerning quenching of acrylic and methacrylic acids is hereby incorporated and forms part of the present disclosure. It is preferred according to the invention that the gas phase is cooled to temperatures between 40 and 80° C. and washed with water and/or condensate from the quenching step to obtain an aqueous solution comprising (meth)acrylic acid, which can also comprise varying amounts of impurities such as acetic acid, maleic acid, fumaric acid, citraconic acid, acrylic acid and formic acid, as well as aldehydes such as formaldehyde, acetaldehyde, propionaldehyde, acrolein, methacrolein, ketones and unreacted C4 compounds. These impurities, as well as water, need to be separated to the greatest extent possible from the (meth)acrylic acid in order to obtain a high degree of purity of (meth)acrylic acid.

In a preferred embodiment of the process according to the invention, process step b) comprises process steps b1.1) extraction of the (meth)acrylic acid from the aqueous (meth)acrylic acid solution via an organic extraction agent to obtain an aqueous phase and an organic phase followed by
b1.2) separation of the organic extraction agent from the organic phase by means of at least one thermal separation process to obtain a crude (meth)acrylic acid-comprising bottom product.

The extraction of the (meth)acrylic acid from the aqueous (meth)acrylic acid-comprising solution occurs in process step b1.1) via an organic extraction agent, for example at least one organic solvent, preferably at least one organic solvent which is substantially immiscible with water, such that an aqueous phase and an organic phase can be formed. Preferred organic solvents which can be used in step b) of the process according to the invention have a boiling point different to, preferably lower than, the boiling point of (meth)acrylic acid. Preferably, in the process according to the invention, the organic extraction agent used in process step b1.1) has a boiling point of less than 161° C. measured at atmospheric pressure. The organic extraction agent can then in principle be separated from (meth)acrylic acid, for example by distillation, preferably at least partially, preferably to a substantial extent in step b1.2) of the process according to the invention, where it can be at least partially removed as a low boiler at a higher level in the distillation apparatus than the pure (meth)acrylic acid. The separated organic extraction agent can be conducted back to process step b1.1), optionally after at least one cooling and/or purification step. Preferred organic solvents for this step are in particular selected from alkanes and aromatic, preferably alkylaromatic, hydrocarbons, whereby at least one organic solvent selected from heptane, toluene and xylene is particularly preferred and heptane, preferably n-heptane is most preferred. The extraction can be carried out by any means known and appearing suitable to the skilled person, for example by means of a washing column, a phase separator or other device suitable for separation of an organic phase from an aqueous phase. At least a part, preferably at least 50 wt %, preferably at least about 70 wt %, preferably at least about 80 wt %, more preferably at least about 90 wt % of the (meth)acrylic acid comprised in the aqueous (meth)acrylic acid solution is extracted into the organic phase.

In step b1.2) of this embodiment of the process according to the invention, the organic extraction agent is at least partially separated from the organic phase by means of a thermal separation process. Suitable thermal separation processes are known to the skilled person, whereby distillation, rectification and the like are preferred according to the invention. One or more separation processes can be carried out according to the invention. In a distillation step, components boiling at temperatures lower than (meth)acrylic acid are removed, preferably removed at the head of a distillation column, or at appropriate levels of a fractionation column or a rectification column, and a bottom phase rich in (meth)acrylic acid is obtained. Lower boiling components to be removed preferably overhead can be, in addition to the organic extraction agent, side products such as those mentioned above, as well as unreacted C4 compound or compounds. It is further possible to at least partially recover unreacted C4 compound or compounds by washing the column exit gas with water at low temperatures or by stripping it with air or inert gases. Recovered unreacted C4 compound or compounds can then be conducted back to the gas phase oxidation, in order to achieve as high a conversion as possible.

In another preferred embodiment of the process according to the invention, process step b) comprises process steps
b2.1) crystallisation of the (meth)acrylic acid from the aqueous (meth)acrylic acid solution, b2.2) optionally, washing of the crystallised (meth)acrylic acid, b2.3) melting of the crystallised (meth)acrylic acid to obtain a crude (meth)acrylic acid-comprising product.

The crystallisation in step b2.1) can occur by methods known to the skilled person for continuous or batchwise, preferably continuous crystallisation, such as dynamic or static crystallisation or a combination of the two, for example melt crystallisation, scratch cooling crystallisation, fractional crystallisation, layer crystallisation, suspension crystallisation, falling film crystallisation and the like, or any combination of two or more thereof, whereby melt crystallisation is preferred. If a melt crystallisation is carried out in the process according to the invention, it is preferred that the crystallisation occurs in at least one crystallisation and melting cycle. In a preferred aspect of a melt crystallisation according to the invention, at least a part of the melted crystallised (meth)acrylic acid is used to wash the crystallised (meth)acrylic acid. Suitable processes are described, for ex-ample, in WO 02/055469, WO 99/14181, WO 01/77056, U.S. Pat. No. 5,504,247, whose disclosure concerning crystallisation is hereby incorporated by reference and forms part of the present disclosure In step c) of the process according to the invention, the crude (meth)acrylic acid-comprising product obtained in step b) is subjected to a further thermal separation process to separate a pure (meth)acrylic acid. By pure (meth)acrylic acid is meant a (meth)acrylic acid which comprises less than 1 wt %, preferably less than 0.5 wt %, more preferably less than 0.3 wt % impurities, based on the total weight of (meth)acrylic acid and impurities. The thermal separation is preferably a distillation, whereby impurities with boiling points higher than (meth)acrylic acid remain in the bottom product and pure (meth)acrylic acid is preferably removed at a level which is higher than the bottom of the column. It is also possible to remove (meth)acrylic acid phases at the top and/or bottom of the column. The amount of impurities comprised in the respective (meth)acrylic acid phases determines whether they are considered to be pure (meth)acrylic acid according to the invention.

In a preferred aspect of the process according to the invention, the crude (meth)acrylic acid-comprising product introduced into process step c) comprises at most 95 wt %, preferably at most 90 wt %, yet more preferably at most 85 wt %, (meth)acrylic acid. For example, if the organic phase obtained in process step b1.1) according to the invention does not have a (meth)acrylic acid concentration which is suitable according to this aspect of the invention, it is possible to adjust this concentration prior to the thermal separation process of step b1.2) of the process according to the invention, for example by addition or removal, preferably removal, of phase components. This can be done, for example, by means of intermediate separation steps, for example distillation to remove low boilers or high boilers, filtration to remove solid impurities, crystallisation, and the like.

In a further preferred aspect of the process according to the invention, the crude methacrylic acid-comprising product introduced into process step c) has an American Public Health Association (APHA) number according to DIN ISO 6271 of 100-250, preferably 250-500 and yet more preferably 500-1000. The APHA number, also referred to as the Platinum-Cobalt Colour Number or the Hazen number, provides a measurement standard for colouration of a solution or liquid with respect to a colour standard platinum-cobalt comparison solution and is typically used to characterise the yellowness of a material, whereby a higher APHA number indicates a greater degree of yellow colouration. More details concerning APHA numbers are provided in "The Measurement of Appearance", 2d ed., Richard S. Hunter and Richard W. Harold, Wiley, 1987, p. 211 and 214, and in U.S. Pat. No. 7,002,035 B2, whose disclosure is hereby introduced by reference and forms part of the disclosure of the present invention.

In a preferred embodiment of the process according to the invention, in process step c) the pure (meth)acrylic acid is separated by means of rectification from the crude (meth)acrylic acid-comprising product, whereby the pure (meth)acrylic acid is removed in a side outlet from the column used for the rectification.

It is preferred in this embodiment of the process according to the invention that the rectification in process step c) is carried out at a bottom pressure from 0.1-100 mbar, preferably from 1 to 80 mbar, and more preferably from 10 to 50 mbar. This pressure range, which is lower than atmospheric pressure, enables the use of lower temperatures for the rectification, making the process gentler, thereby reducing the degree of oligomerisation and polymerisation of (meth)acrylic acid and potentially leading to increased yield with savings in energy expenditure and reduced amount of polymerisation inhibitor and/or stabiliser necessary.

It is further preferred in this aspect of the process according to the invention that the rectification in process step c) is carried out at a bottom temperature from 40-200° C., preferably from 50-140° C., more preferably from 50-100° C. In a particularly preferred embodiment of this aspect of the process according to the invention, the rectification in process step c) is carried out at a bottom temperature of less than 90° C.

It is particularly preferred according to the invention that the pure (meth)acrylic acid in process step c) is removed at a height between the lower fourth and the upper fourth of the rectification column, preferably by means of a side outlet. This allows an improved separation from impurities boiling at higher and lower temperatures than (meth)acrylic acid. Other (meth)acrylic acid fractions can also be removed at different heights, as well as from the head and/or the bottom of the column. Such other (meth)acrylic acid fractions, even if they have impurity content such that they are not considered as pure (meth)acrylic acid according to the invention, can be generally suitable for applications or further processing reactions where a very high (meth)acrylic acid purity is not necessary, or where separation from impurities can be carried out at a later stage without significant difficulties, for example if a desired further processing end or intermediate product has a significantly different melting or boiling point or solubility compared to any impurities present.

Preferably, in the process according to the invention, the amount of pure (meth)acrylic acid removed at a side outlet of the rectification column, in a defined time interval, is 40-80%, preferably 50-80%, more preferably 60-80% of the amount of crude (meth)acrylic acid-comprising product from process step b) which is introduced into the rectification column in the same time interval. The remaining amount of (meth)acrylic acid comprised in the respective amount of crude (meth)acrylic acid-comprising product from process step b) supplied to the rectification column in the same respective time interval is preferably withdrawn at the head and/or the bottom of the rectification column.

The pure (meth)acrylic acid derived in process step c) is further treated in process step d) with an cationic ion-exchange resin. Purification processes via ion-exchange resins are known state-of-the-art. They can be carried out batchwise or continuously. According to the invention a continuous column- or fluid-bed process is preferred. The cationic ion-exchange resin has a preferred loading of 0.5-8 eq./kg, more preferably of 2-6 eq./kg, and most preferred of 4-5 eq./kg. Such ion-exchange resins are commercially available, for instance, from Rohm & Haas under the trade name Amberlyst®. In a preferred embodiment of the invention the ion-exchange resin is dried prior to use.

The ion-exchange treatment according to process d) is carried out at temperatures between 30-100° C., preferably between 50-90° C. and more preferably between 60-80° C. The weight ratio of ion-exchange resin to pure (meth)acrylic acid in process step d) is 0.1-10%, preferably 0.3-8%, more preferably 0.5-5%. The residence time of pure (meth)acrylic acid within the ion-exchange process step d) is 1-100 min, preferably 5-80 min, more preferably 10-70 min.

The purified (meth)acrylic acid from step d) is subject to further distillation in process step e) to generate highly-pure (meth)acrylic acid. Highly-pure (meth)acrylic acid in the context of the invention is defined as (meth)acrylic acid showing an APHA value of less than 50 after an addition of triethylamine (ratio acid:amine=9:1) and storage at room temperature for 3 days. The simple distillation process step e) does not require a separation column. The distillation is carried out at a pressure of 10-50 mbar, more preferred at 10-20 mbar and temperatures between 30-80° C., preferred at 50-70° C. The highly-purified (meth)acrylic acid is withdrawn as head-product, 5-20%, preferred 5-10%, are withdrawn as bottom-product.

The following examples are intended to illustrate the invention, but not to limit it in any way:

COMPARATIVE EXAMPLE 1

Pure methacrylic acid generated from process step c) was mixed with triethylamine (NEt3) in a ratio of acid:amine=9:1 and stored at room temperature. The APHA values according to DIN ISO 6271 were measured at different times (see Tab. 1).

COMPARATIVE EXAMPLE 2

The ion-exchange resin Amberlyst®15, purchased from Rohm & Haas, was dried to constant weight at 65° C. for 36 hours. Pure methacrylic acid generated from process step c) was mixed with the dried ion-exchange resin at a ratio of 100:5 and stirred for 1 h at 75° C. Afterwards, the mixture was filtered and the filtrate mixed with NEt3 in a ration of 9:1. APHA values of the filtrate were measured according to Comparative Example 1.

EXAMPLE 1

This example was carried out similar to Comparative Example 2, with the difference that instead of a filtration after the ion-exchange treatment a distillation was performed according to process step e).

COMPARATIVE EXAMPLE 3

This example was carried out according to Example 1, however, with a ratio of methacrylic acid to ion-exchanger of only 100:0,05. The APHA values are shown in Tab.2

EXAMPLES 2-4

These examples were carried out according to Example 1, however, with different ratios of methacrylic acid to ion-exchanger as shown in Tab. 2

COMPARATIVE EXAMPLE 4

This example was carried out according to Example 1, however, the treatment temperature with the ion-exchange resin was room temperature instead of 75° C. (see Tab.3).

EXAMPLES 5-6

These examples were carried out according to Example 1, however, with ion-exchange treatment temperatures as indicated in Tab. 3.

EXAMPLES 7-9

These examples were carried out according to Example 1, however, with different ion-exchange treatment times as indicated in Tab. 4.

TABLE 1

APHA values

| | \multicolumn{4}{c}{Time after mixing with NEt3} |
|---|---|---|---|---|
| | Start | 1 hour | 2-3 days | 1-2 weeks |
| Comp. Exam. 1 | 7 | 94 | 156 | 189(8 d) |
| Comp. Exam. 2 | 18 | 18 | 65(3 d) | 82(7 d) |
| Example 1 | 5 | 5 | 10(3 d) | 23(7 d) |

TABLE 2

Different ratios of ion-exchanger

| | | Time after mixing with NEt3 | | | |
|---|---|---|---|---|---|
| | Ratio MAA/Ion-Exchanger | Start | 1 hour | 1 day | 2-3 days | 5-6 days |
| Comp. Exam. 3 | 100/0.05 | 7 | 46 | 70 | 130 | 144 |
| Example 2 | 100/0.1 | 8 | 20 | 35 | 48 | 80 |
| Example 3 | 100/0.5 | 7 | 14 | 21 | 25 | 45 |
| Example 4 | 100/5 | 5 | 5 | 8 | 10 | 23 |

TABLE 3

Different treatment temperatures

| | | Time after mixing with NEt3 | | | |
|---|---|---|---|---|---|
| | Treatment Temperature (° C.) | Start | 1 hour | 1 day | 2-3 days | 5-6 days |
| Comp. Exam. 4 | 23(RT) | 7 | 55 | 90 | 115 | |
| Example 5 | 50 | 7 | 20 | 32 | 45 | |
| Example 6 | 75 | 7 | 14 | 21 | 25 | 45 |

TABLE 4

Different treatment intervals

| | | Time after mixing with NEt3 | | | |
|---|---|---|---|---|---|
| | Treatment Interval (min) | Start | 1 hour | 1 day | 2-3 days | 5-6 days |
| Example 7 | 10 | 8 | 21 | 38 | 49 | |
| Example 8 | 30 | 7 | 12 | 22 | 35 | |
| Example 9 | 60 | 7 | 12 | 18 | 21 | 33 |

The invention claimed is:

1. A process for preparing highly pure, non-yellowing (meth)acrylic acid, comprising:
   a) condensing a (meth)acrylic acid-containing gas phase obtained via a gas phase oxidation process of a C4-compound to generate an aqueous (meth)acrylic acid solution;
   b) separating the (meth)acrylic acid from the aqueous (meth)acrylic acid solution to obtain crude (meth)acrylic acid;
   c) rectifying the crude (meth)acrylic acid in a rectification column to obtain pure (meth)acrylic acid via a sidestream outlet of the rectification column;
   d) treating the pure (meth)acrylic acid generated in c) with an ion exchange resin; and
   e) distilling the (meth)acrylic acid generated in d).

2. The process of claim 1, wherein b) comprises extracting the aqueous (meth)acrylic acid solution via an organic solvent followed by a thermal separation process to obtain the crude (meth)acrylic acid.

3. The process of claim 1, wherein the crude (meth)acrylic acid introduced into c) exhibits an APHA value according to DIN ISO 6271 of 100-250.

4. The process of claim 1, wherein in c) the amount of pure (meth)acrylic acid removed via the sidestream outlet in a defined time interval is 40-80% of the amount of crude (meth)acrylic acid introduced into the rectification column in the same time interval.

5. The process of claim 1, wherein the ion exchange resin is dried prior to use.

6. The process of claim 1, wherein d) is carried out continuously.

7. The process of claim 1, wherein the treating in d) is carried out at a temperature of 30-100° C.

8. The process of claim 1, wherein a weight ratio of ion-exchange resin to pure (meth)acrylic acid is 0.1-10%.

9. The process of claim 1, wherein a residence time of pure (meth)acrylic acid within d) is 1-100 min.

* * * * *